US010781212B2

(12) United States Patent
Durham

(10) Patent No.: US 10,781,212 B2
(45) Date of Patent: Sep. 22, 2020

(54) 2,6-DIAMINO PYRIDINE COMPOUNDS

(71) Applicant: Eli Lilly and Company, Indianapolis, IN (US)

(72) Inventor: Timothy Barrett Durham, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/555,075

(22) Filed: Aug. 29, 2019

(65) Prior Publication Data

US 2020/0071331 A1    Mar. 5, 2020

Related U.S. Application Data

(60) Provisional application No. 62/726,520, filed on Sep. 4, 2018.

(51) Int. Cl.
C07D 471/14    (2006.01)

(52) U.S. Cl.
CPC .................................. *C07D 471/14* (2013.01)

(58) Field of Classification Search
None
See application file for complete search history.

(56) References Cited

U.S. PATENT DOCUMENTS 9,809,579 B2 * 11/2017 Dowling .............. C07D 403/04
2017/0183328 A1    6/2017 Dowling et al.

OTHER PUBLICATIONS

Cirillo, P., Gersch, M. S., Mu, W., Scherer, P. M., Kim, K. M., Gesualdo, L., . . . & Sautin, Y. Y. (2009). Ketohexokinase-dependent metabolism of fructose induces proinflammatory mediators in proximal tubular cells. Journal of the American Society of Nephrology, 20(3), 545-553.
Ishimoto, T., Lanaspa, M. A., Le, M. T., Garcia, G. E., Diggle, C. P., MacLean, P. S., . . . & Rivard, C. J. (2012). Opposing effects of fructokinase C and A isoforms on fructose-induced metabolic syndrome in mice. Proceedings of the National Academy of Sciences, 109(11), 4320-4325.

Vos, M. B., & Lavine, J. E. (2013). Dietary fructose in nonalcoholic fatty liver disease. Hepatology, 57(6), 2525-2531.
Softic, S., Gupta, M. K., Wang, G X., Fujisaka, S., O'neill, B. T., Rao, T. N., . . . & Newgard, C. S. (2017) Divergent effects of glucose and fructose on hepatic lipogenesis and insulin signaling. The Journal of clinical investigation, 127(11), 4059-4074.
Mirtschink, P., Jang, C., Arany, Z., Krek, W., (2018). Fructose metabolism, cardiometabolic risk, and the epidemic of coronary artery disease, European Heart Journal, vol. 39, Issue 26, Jul. 7, 2018, pp. 2497-2505.
Hannou, S.A., et al., "Fructose Metabolism and Metabolic Disease," J. Clin. Invest., (2018), 128(2), 544-555.
International Search Report of the International Searching Authority pertaining to International Application No. PCT/US2019/048788; dated Dec. 17, 2019; 5 pages.
Written Opinion of the International Searching Authority pertaining to International Application No. PCT/US2019/048788; dated Dec. 17, 2019; 8 pages.
Maryanoff, B. E., O'Neill, J. C., McComsey, D. F., Yabut, S. C., Luci, D. K., Jordan Jr, A. D., . . . & Petrounia, I. (2011). Inhibitors of ketohexokinase: discovery of pyrimidinopyrimidines with specific substitution that complements the ATP-binding site. ACS medicinal chemistry letters, 2(7), 538-543.
Huard, K., Ahn, K., Amor, P., Beebe, D. A., Borzilleri, K. A., Chrunyk, B. A., . . . & Dowling, M. S. (2017). Discovery of fragment-derived small molecules for in vivo inhibition of ketohexokinase (KHK). Journal of medicinal chemistry, 60(18), 7835-7849.

* cited by examiner

*Primary Examiner* — Kamal A Saeed
(74) *Attorney, Agent, or Firm* — Macharri Vorndran-Jones

(57) ABSTRACT

The present invention provides a compound of Formula I:

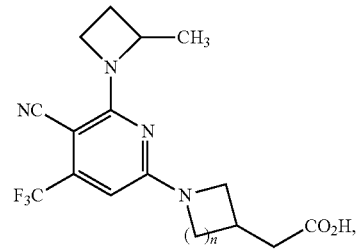

or a pharmaceutically acceptable salt thereof, and the use of compounds of Formula I for treating metabolic conditions, such as type 2 diabetes mellitus, heart failure, diabetic kidney disease, and non-alcoholic steatohepatitis.

12 Claims, No Drawings

2,6-DIAMINO PYRIDINE COMPOUNDS

The present invention relates to novel ketohexokinase (KHK) inhibitor compounds, to pharmaceutical compositions comprising the compounds and to the use of the compounds for the treatment of certain metabolic conditions, such as type 2 diabetes mellitus (T2DM), heart failure, diabetic kidney disease and non-alcoholic steatohepatitis (NASH).

Metabolic syndrome is commonly defined as a clustering of conditions that reflect over nutrition and a sedentary lifestyle and its manifestations include T2DM, non-alcoholic fatty liver disease (NAFLD), obesity, dyslipidemia, heart failure and kidney disease.

T2DM is characterised by relative insulin deficiency caused by pancreatic β-cell dysfunction and insulin resistance in target organs. It accounts for more than 90% of patients with diabetes and leads to microvascular and macrovascular complications that cause profound psychological and physical distress to patients while placing a huge burden on health-care systems (Davies, M. J., et al.; *Lancet*, 389, 2239-2251, 2017).

Heart failure is a syndrome caused by structural or functional cardiac abnormalities that lead to elevated intracardiac pressures or a reduced cardiac output at rest or during stress. Heart failure is a leading and increasing cause of morbidity and mortality worldwide (Teerlink, J. R., et al.; *Lancet*, 390, 1981-1995, 2017).

Diabetic kidney disease develops in nearly half of patients with T2DM and is the leading cause of chronic kidney disease worldwide. Metabolic changes associated with diabetes leads to glomerular hyperfiltration, progressive albuminuria, declining glomerular filtration rate and ultimately end-stage renal disease (Alicic, R. Z., et al.; *Clin. J. Am. Soc. Nephrol.*, 12: 2032-2045, 2017).

NAFLD represents a spectrum of liver disease that can lead to progressive NASH, fibrosis, and ultimately hepatocellular carcinoma and liver failure. It is estimated that in the next 20 years, NAFLD will become the major cause of liver-related morbidity and mortality as well as the leading indication for liver transplantation (Bertot, L. C., et al.; *Int. J. Mol. Sci.*, 17(5), 774, 2016).

KHK, also referred to as fructokinase, is the rate-limiting enzyme involved in fructose metabolism. It catalyses the phosphorylation of fructose to fructose-1-phosphate (F1P), causing concomitant depletion of cellular ATP levels. In contrast to glucose, fructose metabolism lacks feedback inhibition and it triggers accumulation of downstream intermediates involved in, for example, lipogenesis, gluconeogenesis and oxidative phosphorylation (Hannou, S. A., et al.; *J. Clin. Invest.*, 128(2), 544-555, 2018). This has negative metabolic consequences which are associated with a number of serious metabolic disorders.

KHK exists in two alternatively spliced isoforms consisting of KHK-C and KHK-A differing in exon 3. KHK-C is expressed primarily in the liver, kidney and intestine, whereas KHK-A is more ubiquitous. Mice deficient in both isoforms are fully protected from fructose-induced metabolic syndrome. However, the adverse metabolic effects are exacerbated in mice lacking KHK-A only (Ishimoto T, et al.; *Proc. Natl. Acad. Sci. USA*, 109(11), 4320-4325, 2012).

Several epidemiologic and experimental studies have reported that increased consumption of fructose, and more precisely increased fructose metabolism, may play an important role in the development of metabolic syndrome, in particular in the development of T2DM (Softic et al.; *J. Clin. Invest.*, 127(11), 4059-4074, 2017), heart failure (Mirtschink, P., et al.; *Eur. Heart J.*, 39, 2497-2505, 2018), diabetic kidney disease (Cirillo, P., et al.; *J. Am. Soc. Nephrol.*, 20, 545-553, 2009) and NAFLD/NASH (Vos, M. B., et al.; *Hepatology*, 57, 2525-2531, 2013). Targeting inhibition of KHK is expected to limit fructose metabolism and provide effective treatment options for a number of metabolic disorders.

US 2017/0183328 A1 discloses substituted 3-azabicyclo [3.1.0]hexanes as KHK inhibitors.

There is a need for alternate treatments for metabolic syndrome and associated indications including T2DM, heart failure, diabetic kidney disease and NASH. In particular, there is a need for compounds having KHK inhibitory activity to provide treatment options for these diseases. There is a furthermore a need for potent KHK inhibitors having properties which are important to the therapeutic use in humans, such as oral bioavailability and a half-life sufficient to support daily dosing, or a limited drug-drug interaction profile.

Accordingly, the present invention provides a compound of Formula I:

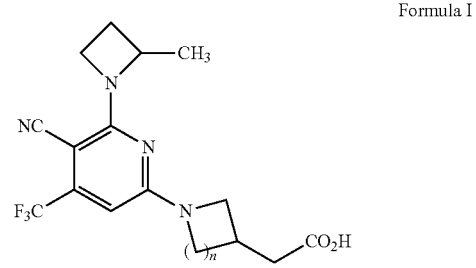

Formula I wherein n is 1 or 2;
or a pharmaceutically acceptable salt thereof.

Formula I includes all individual enantiomers and diastereomers thereof, as well as mixtures of enantiomers and racemates.

In a particular embodiment, a compound of the invention is a compound of the formula:

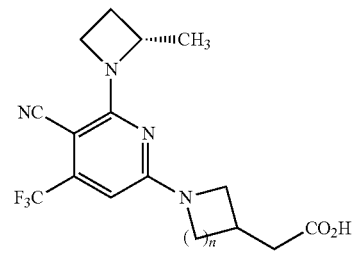

or a pharmaceutically acceptable salt thereof.
In one embodiment, n is 1. In this embodiment, a compound of the invention is a compound of the formula:

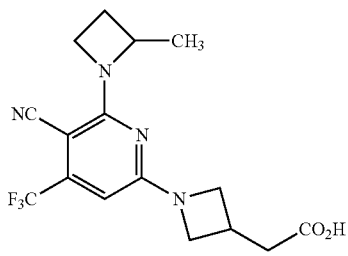

or a pharmaceutically acceptable salt thereof. In a preferred embodiment, a compound of the invention is a compound of the formula:

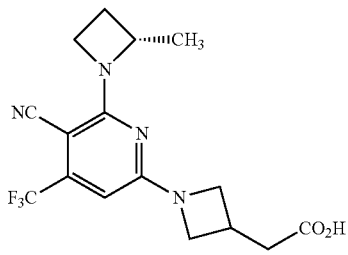 [SMILES: C[C@H]1CCN1c1nc(N2CC(CC(=O)O)C2)cc(C(F)(F)F)c1C#N]

or a pharmaceutically acceptable salt thereof.

In another embodiment, n is 2. In this embodiment, a compound of the invention is a compound of the formula:

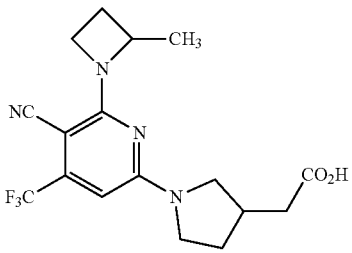 [SMILES: CC1CCN1c1nc(N2CCC(CC(=O)O)C2)cc(C(F)(F)F)c1C#N]

or a pharmaceutically acceptable salt thereof. In a preferred embodiment, a compound of the invention is a compound of the formula:

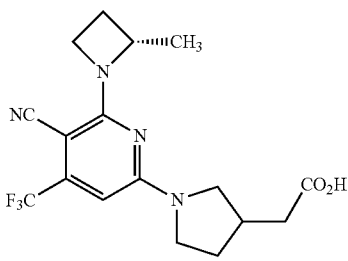 [SMILES: C[C@H]1CCN1c1nc(N2CCC(CC(=O)O)C2)cc(C(F)(F)F)c1C#N]

or a pharmaceutically acceptable salt thereof. In a further preferred embodiment, a compound of the invention is a compound of the formula:

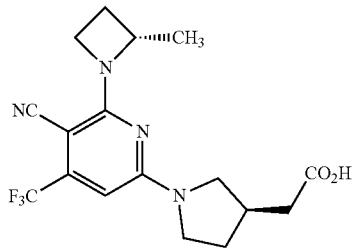 [SMILES: C[C@H]1CCN1c1nc(N2CC[C@H](CC(=O)O)C2)cc(C(F)(F)F)c1C#N]

or a pharmaceutically acceptable salt thereof. In this embodiment, the compound of the invention is 2-[(3R)-1-[5-cyano-6-[(2S)-2-methylazetidin-1-yl]-4-(trifluoromethyl)-2-pyridyl]pyrrolidin-3-yl]acetic acid or a pharmaceutically acceptable salt thereof.

In an embodiment, the present invention also provides a method of treating T2DM in a patient in need of such treatment comprising administering to the patient an effective amount of a compound of Formula I, or a pharmaceutically acceptable salt thereof. In a preferred embodiment, the method comprises administering 2-[(3R)-1-[5-cyano-6-[(2S)-2-methylazetidin-1-yl]-4-(trifluoromethyl)-2-pyridyl]pyrrolidin-3-yl]acetic acid, or a pharmaceutically acceptable salt thereof.

In an embodiment, the present invention also provides a method of treating heart failure in a patient in need of such treatment comprising administering to the patient an effective amount of a compound of Formula I, or a pharmaceutically acceptable salt thereof. In a preferred embodiment, the method comprises administering 2-[(3R)-1-[5-cyano-6-[(2S)-2-methylazetidin-1-yl]-4-(trifluoromethyl)-2-pyridyl]pyrrolidin-3-yl]acetic acid, or a pharmaceutically acceptable salt thereof.

In an embodiment, the present invention also provides a method of treating diabetic kidney disease in a patient in need of such treatment comprising administering to the patient an effective amount of a compound of Formula I, or a pharmaceutically acceptable salt thereof. In a preferred embodiment, the method comprises administering 2-[(3R)-1-[5-cyano-6-[(2S)-2-methylazetidin-1-yl]-4-(trifluoromethyl)-2-pyridyl]pyrrolidin-3-yl]acetic acid, or a pharmaceutically acceptable salt thereof.

In an embodiment, the present invention also provides a method of treating NASH in a patient in need of such treatment comprising administering to the patient an effective amount of a compound of Formula I, or a pharmaceutically acceptable salt thereof. In a preferred embodiment, the method comprises administering 2-[(3R)-1-[5-cyano-6-[(2S)-2-methylazetidin-1-yl]-4-(trifluoromethyl)-2-pyridyl]pyrrolidin-3-yl]acetic acid, or a pharmaceutically acceptable salt thereof.

In an embodiment, the present invention also provides a method of treating chronic kidney disease in a patient in need of such treatment comprising administering to the patient an effective amount of compound of Formula I, or a pharmaceutically acceptable salt thereof. In a preferred embodiment, the method comprises administering 2-[(3R)-1-[5-cyano-6-[(2S)-2-methylazetidin-1-yl]-4-(trifluoromethyl)-2-pyridyl]pyrrolidin-3-yl]acetic acid, or a pharmaceutically acceptable salt thereof.

In an embodiment, the present invention further provides a method of treating a disease selected from the group consisting of metabolic syndrome, NAFLD, obesity, diabetic complications for example diabetic retinopathy, cardiovascular disease, coronary artery disease, and dyslipidemia, in a patient in need of such treatment, comprising administering to the patient an effective amount of a compound of Formula I, or a pharmaceutically acceptable salt thereof. In a preferred embodiment, the method comprises administering 2-[(3R)-1-[5-cyano-6-[(2S)-2-methylazetidin-1-yl]-4-(trifluoromethyl)-2-pyridyl]pyrrolidin-3-yl]acetic acid, or a pharmaceutically acceptable salt thereof.

Furthermore, in an embodiment, this invention provides a compound of Formula I, or a pharmaceutically acceptable salt thereof, for use in therapy. In a particular embodiment, the present invention provides a compound of Formula I, or a pharmaceutically acceptable salt thereof, for use in treating T2DM. In a particular embodiment, the present invention provides a compound of Formula I, or a pharmaceutically acceptable salt thereof, for use in treating heart failure. In a particular embodiment, the present invention provides a compound of Formula I, or a pharmaceutically acceptable salt thereof, for use in treating diabetic kidney disease. In a particular embodiment, the present invention provides a compound of Formula I, or a pharmaceutically acceptable salt thereof, for use in treating NASH. In a particular embodiment, the present invention also provides a compound of Formula I, or a pharmaceutically acceptable salt thereof, for use in treating chronic kidney disease. In an embodiment, the invention also provides a compound of Formula I, or a pharmaceutically acceptable salt thereof, for use in treating metabolic syndrome, NAFLD, obesity, diabetic complications for example diabetic retinopathy, cardiovascular disease, coronary artery disease, or dyslipidemia. In a preferred embodiment, the compound of Formula I in the therapeutic uses above is 2-[(3R)-1-[5-cyano-6-[(2S)-2-methylazetidin-1-yl]-4-(trifluoromethyl)-2-pyridyl]pyrrolidin-3-yl]acetic acid, or a pharmaceutically acceptable salt thereof.

Furthermore, in an embodiment, this invention provides the use of a compound of Formula I, or a pharmaceutically acceptable salt thereof, for the manufacture of a medicament for treating T2DM. In an embodiment, the present invention provides the use of a compound of Formula I, or a pharmaceutically acceptable salt thereof, for the manufacture of a medicament for treating heart failure. In an embodiment, the present invention provides the use of a compound of Formula I, or a pharmaceutically acceptable salt thereof, for the manufacture of a medicament for treating diabetic kidney disease. In an embodiment, the present invention provides the use of a compound of Formula I, or a pharmaceutically acceptable salt thereof, for the manufacture of a medicament for treating NASH. In an embodiment, the present invention provides the use of a compound of Formula I, or a pharmaceutically acceptable salt thereof, for the manufacture of a medicament for treating chronic kidney disease. In an embodiment, the invention also provides the use of a compound of Formula I, or a pharmaceutically acceptable salt thereof, for the manufacture of a medicament for treating metabolic syndrome, NAFLD, obesity, diabetic complications for example diabetic retinopathy, cardiovascular disease, coronary artery disease, or dyslipidemia. In a preferred embodiment, the compound of Formula I is 2-[(3R)-1-[5-cyano-6-[(2S)-2-methylazetidin-1-yl]-4-(trifluoromethyl)-2-pyridyl]pyrrolidin-3-yl]acetic acid, or a pharmaceutically acceptable salt thereof.

In an embodiment, the invention further provides a pharmaceutical composition comprising a compound of Formula I, or a pharmaceutically acceptable salt thereof, with one or more pharmaceutically acceptable carriers, diluents, or excipients. In an embodiment, the invention further provides a process for preparing a pharmaceutical composition comprising admixing a compound of Formula I, or a pharmaceutically acceptable salt thereof, with one or more pharmaceutically acceptable carriers, diluents, or excipients.

As used herein, the terms "treating" or "to treat" includes restraining, slowing, stopping, or reversing the progression or severity of an existing symptom or disorder.

As used herein, the term "patient" refers to a mammal. Preferably, the patient is human.

As used herein, the term "effective amount" refers to the amount or dose of a compound of Formula I, or a pharmaceutically acceptable salt thereof, which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. The compounds of the present invention are effective at a dosage per day that falls within the range of about 0.1 to about 15 mg/kg of body weight.

The compounds of the present invention are formulated as pharmaceutical compositions administered by any route which makes the compound bioavailable. Preferably, such compositions are for oral administration. Such pharmaceutical compositions and processes for preparing same are well known in the art (See, e.g., Remington, J. P., "*Remington: The Science and Practice of Pharmacy*", L. V. Allen, Editor, 22$^{nd}$ Edition, Pharmaceutical Press, 2012).

The compounds of Formula I and the pharmaceutically acceptable salts thereof are particularly useful in the treatment methods of the invention, with certain configurations being preferred. The following list of compounds of the present invention describe such configurations. It will be understood that these preferences are applicable to the compounds of the invention, as well as the treatment methods, therapeutic uses and pharmaceutical compositions.

Compounds of the present invention include:

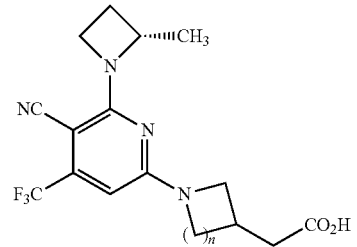

Formula Ia

Formula Ib

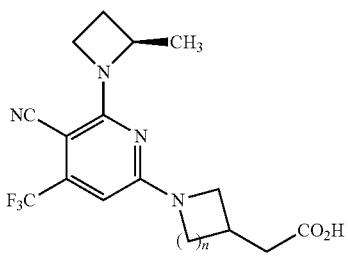

and pharmaceutically acceptable salts thereof.

Further compounds of the present invention include:

Formula IIa

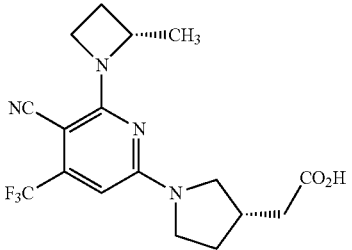

Formula IIb

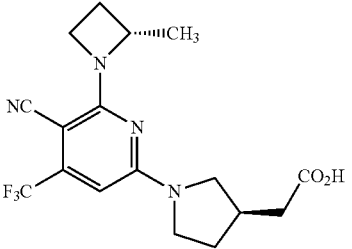

and pharmaceutically acceptable salts thereof.

Further compounds of the present invention include:

Formula IIIa'

Formula IIIa"

Formula IIIb'

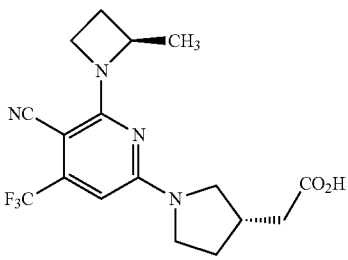

Formula IIIb"

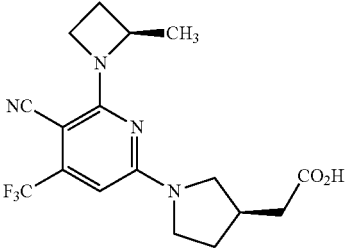

and pharmaceutically acceptable salts thereof.

Although the present invention contemplates all individual enantiomers and diasteromers, as well as mixtures thereof, including racemates, compounds of Formula Ia, Formula IIa and IIIa", and pharmaceutically acceptable salts thereof, are particularly preferred.

Individual enantiomers may be separated or resolved by one of ordinary skill in the art at any convenient point in the synthesis of compounds of the invention, by methods such as selective crystallization techniques, chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994), or supercritical fluid chromatography (SFC) (See for example, T. A. Berger; "*Supercritical Fluid Chromatography Primer*," Agilent Technologies, July 2015).

A pharmaceutically acceptable salt of the compounds of the invention can be formed, for example, by reaction of an appropriate neutral form of a compound of the invention and an appropriate pharmaceutically acceptable acid or base in a suitable solvent under standard conditions well known in the art (See, for example, Bastin, R. J., et al.; *Org. Process. Res. Dev.*, 4, 427-435, 2000 and Berge, S. M., et al.; *J. Pharm. Sci.*, 66, 1-19, 1977).

The compounds of the present invention, or salts thereof, may be prepared by a variety of procedures known to one of ordinary skill in the art, some of which are illustrated in the schemes, preparations, and examples below. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention. In addition, one of ordinary skill in the art appreciates that compounds of Formula I may be prepared by using starting material or intermediate with the corresponding desired stereochemical configuration which can be prepared by one of skill in the art.

Certain abbreviations are defined as follows: "ABT" refers to 1-aminobenzotriazole; "ACN" refers to acetonitrile; "BSA" refers to bovine serum albumin; "CAS #" refers to Chemical Abstracts Registry number; "DCM" refers to methylene chloride or dichloromethane; "DIPEA" refers to diisopropylethylamine; "DMEM" refers to Dulbecco's Modified Eagle's medium; "DMSO" refers to dimethyl sulfoxide; "ELSD" refers to Evaporative light scattering detector; "ES/MS" refers to Electrospray Mass Spectrometry; "EtOAc" refers to ethyl acetate; "EtOH" refers to ethanol or ethyl alcohol; "FBS" refers to fetal bovine serum; "h" refers to hour or hours; "HPLC" refers to high-performance liquid chromatography; "Me" refers to methyl; "MeOH" refers to methanol; "MTBE" refers to methyl-tert-butyl ether; "min" refers to minute or minutes; "m/z" refers to mass-to-charge ratio; "PBS" refers to phosphate buffered saline; "Ph" refers to phenyl; "RBF" refers to round bottom flask; "RT" refers to room temperature; "SCX" refers to selective cation exchange; "SFC" refers to Supercritical Fluid Chromatography; "THF" refers to tetrahydrofuran.

Scheme 1 depicts the general preparation of the compounds of Formula I. In Step 1, 3-cyano-2,6-dichloro-4-(trifluoromethyl)pyridine (1) and a cyclic amine (2) are reacted in the presence of a base, such as NaHCO₃ or DIPEA, in EtOH or MeOH to yield an aminopyridine (3). Alternatively, the reaction solvent for this step can be DCM. In Step 2, compound 3 is reacted with 2-methyl azetidine (4) at elevated temperature and in the presence of a base, such as NaHCO₃ or DIPEA, in EtOH or MeOH to give a diaminopyridine (5). Alternatively, the reaction solvent for this step can be THF. In Step 3, the ester moiety is hydrolysed using a base such as NaOH or LiOH in MeOH or THF at elevated temperature to give a compound of Formula Ia. Alternatively, this step may be performed using the same reagents in a microwave reactor.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to an HPLC which may or may not have an ELSD. LC-MS conditions (low pH): column: PHENOMENEX® GEMINI® NX C18 2.0×50 mm 3.0 µm, 110 Å; gradient: 5-95% B in 1.5 min, then 95% B for 0.5 min column temperature: 50° C.+/−10° C.; flow rate: 1.2 mL/min; 1 µL injection volume; Solvent A: deionized water with 0.1% HCOOH; Solvent B: ACN with 0.1% formic acid; wavelength 200-400 nm and 212-216 nm. If the HPLC is equipped with an ELSD the settings are 45° C. evaporator temperature, 40° C. nebulizer temperature, and 1.6 SLM gas flow rate. Alternate LC-MS conditions (high pH): column: Waters xBridge® C18 column 2.1×50 mm, 3.5 µm; gradient: 5-95% B in 1.5 min, then 95% B for 0.50 min; column temperature: 50° C.+/−10° C.; flow rate: 1.2 mL/min; 1 µL injection volume; Solvent A: 10 mM NH₄HCO₃ pH 9; Solvent B: ACN; wavelength: 200-400 nm and 212-216 nm; if had ELSD: 45° C. evaporator temp, 40° C. nebulizer temp, and 1.60 SLM gas flow rate.

Preparation 1

(2S)-1-Benzhydryl-2-methyl-azetidine [(1R,4S)-7,7-dimethyl-2-oxo-norbornan-1-yl]methanesulfonic Acid Salt

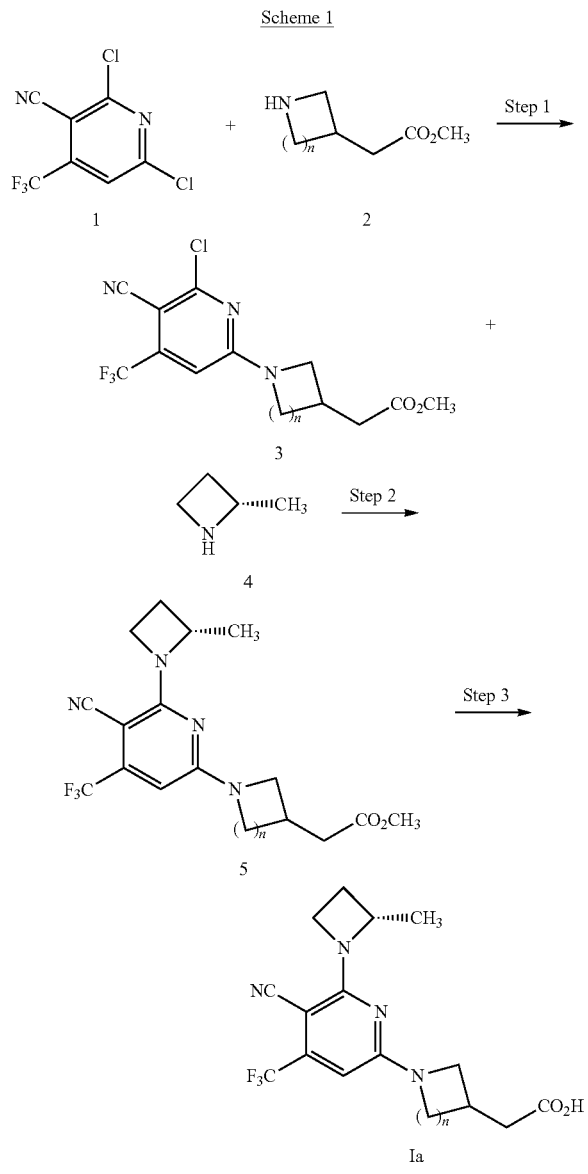

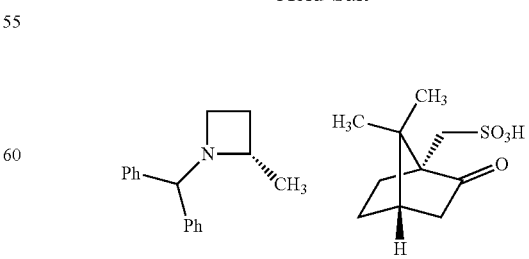

Assemble a 2000 mL 3-neck RBF with an addition funnel, nitrogen inlet and a thermometer adapter. Purge the vessel with nitrogen and add (3R)-butane-1,3-diol (25 g, 277.4 mmol), DIPEA (127 ml, 731 mmol) and ACN (556 ml). Cool to −30° C. Add trifluoromethanesulfonic anhydride (101 mL, 601 mmol) dropwise over 3 h such that the internal temperature is maintained between −35 and −30° C. After the completion of the addition, stir for 10 min at −35 to −30° C. Add trifluoromethanesulfonic anhydride (1.9 mL, 11 mmol) dropwise over 5 min such that the internal temperature is maintained between −35 and −30° C. After the completion of the addition, stir for 10 min at −35 to −30° C. Add DIPEA (127 mL, 731 mmol) dropwise over 15 min such that the internal temperature is maintained between −35 and −30° C. After the completion of the addition, stir for 10 min at −35 to −30° C. In a separate flask under nitrogen, dissolve aminodiphenylmethane (48.0 mL, 270 mmol) in ACN (49 mL, 935 mmol) and transfer the resulting solution to the addition funnel. Add the amine solution to the cold triflate dropwise over 40 min such that the internal temperature is maintained between −20 to −35° C. After the completion of the addition, stir for 30 min at −35 to −30° C. Transfer the reaction to a water bath and allow it to slowly warm over 30 min. Remove the bath and allow the reaction to warm to RT over 30 min. Transfer the vessel to a heating mantle and warm the reaction to 45° C. for 30 min, then cool to RT. Pour the resulting mixture into 1200 mL of water and extract with toluene (400 mL×3). Combine the extracts, wash with water, sat. aq. NaCl solution, dry over anhydrous $Na_2SO_4$, filter and concentrate on a rotary evaporator. Dry the material under vacuum overnight. Dissolve the residue in DCM (400 mL). Prepare a silica pad on a fritted funnel and equilibrate it with 1:1 heptane/EtOAc. Load the product solution onto the silica pad and wash with 1600 mL of 1:1 heptane/EtOAc. Concentrate the filtrate to give a red oil. Dissolve the oil in MeOH (250 mL) and place the flask in a water bath (~10° C.). Add L(−)-camphorsulfonic acid (61.6 g, 265 mmol) portion-wise keeping the internal temperature below 20° C. Stir the resulting mixture for 15 min and then concentrate on a rotary evaporator to give a brown foam. Dry the foam on a vacuum pump for 2 h. Dissolve the foam in 130 mL of DCM. Attach an addition funnel to the flask. Use the funnel to slowly add 1100 mL of EtOAc to the stirring solution. Transfer the resulting mixture to a 4000 mL beaker and stir open to the atmosphere overnight. Cool the beaker in an ice bath for 10 min. Collect the precipitate in a fritted funnel by vacuum filtration washing with a minimal amount of ice-cold EtOAc. Dry the solid on the frit for 2 h. Dissolve the resulting white solid in a minimal amount of DCM, transfer to a 2000 mL beaker and then dilute slowly with EtOAc until the clear solution starts to become cloudy. Stir the suspension for 4 h while open to the atmosphere. Collect the solids by vacuum filtration using a fritted funnel and dry on the frit overnight to give the title compound (111.8 g, 238.06 mmol, 86% Yield) as a white solid. $^1$H NMR (400 MHz, d6-DMSO): 10.54-10.47 (m, 1H), 7.61 (d, J=7.3 Hz, 5H), 7.47-7.37 (m, 7H), 5.85 (d, J=10.3 Hz, 1H), 4.68-4.61 (m, 1H), 3.91-3.83 (m, 2H), 3.37 (s, 8H), 2.99 (d, J=14.6 Hz, 1H), 2.77-2.68 (m, 1H), 2.51-2.44 (m, 4H), 2.30-2.16 (m, 2H), 1.91-1.81 (m, 2H), 1.42-1.28 (m, 3H), 1.08 (s, 3H), 1.01 (d, J=6.6 Hz, 3H), 0.77 (s, 4H); >98% ee [HPLC: Chiralcel OJ (10 cm×4.6 mm, 5 [μm], 5 mL/min, 40° C. isocratic 10% EtOH (0.2% $^i$PrNH$_2$)/CO$_2$].

Preparation 2

[(1R,4 S)-7,7-Dimethyl-2-oxo-norbornan-1-yl]methanesulfonate (2 S)-2-methylazetidin-1-ium Salt

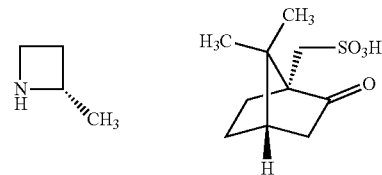

To a 2250 mL Parr vessel add 20 wt % Pd(OH)$_2$ on carbon (6.62 g). Purge the bottle with nitrogen and add 250 mL of MeOH. To the resulting suspension, slowly add (2S)-1-benzhydryl-2-methyl-azetidine [(1R,4S)-7,7-dimethyl-2-oxo-norbornan-1-yl]methanesulfonic acid salt (111 g, 236 mmol) dissolved in 250 mL of MeOH. Seal the vessel. Purge with nitrogen followed by hydrogen and pressurize to 60 PSI. Vigorously shake the reaction vessel in a Parr Shaker apparatus for 15 h at RT. Purge the vessel with nitrogen and then filter the reaction mixture through a pad of celite, washing with MeOH. Concentrate the filtrate to give a white solid and dry under vacuum. Suspend the solid in 780 mL of 1:1 MTBE/EtOAc and heat the mixture to 65° C. for 20 h then cool to RT and stir overnight. Collect the solids by filtration. Suspend the solids in 380 mL of MTBE and stir at RT for 24 h. Collect the white solid by filtration to give the title compound (41.5 g, 136.78 mmol, 58% Yield). $^1$H NMR (400 MHz, d6-DMSO): 8.68-8.55 (m, 1H), 4.51-4.42 (m, 1H), 3.91-3.75 (m, 1H), 3.36 (s, 3H), 2.91 (d, J=14.6 Hz, 1H), 2.69-2.61 (m, 1H), 2.52-2.46 (m, 2H), 2.28-2.22 (m, 1H), 2.17-2.10 (m, 1H), 1.96 (t, J=4.5 Hz, 1H), 1.89-1.79 (m, 1H), 1.43 (d, J=6.7 Hz, 2H), 1.36-1.26 (m, 1H), 1.05 (s, 2H), 0.75 (s, 2H).

Preparation 3

Methyl 2-[(3R)-1-[6-chloro-5-cyano-4-(trifluoromethyl)-2-pyridyl]pyrrolidin-3-yl]acetate

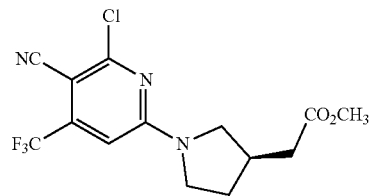 [SMILES: COC(=O)C[C@H]1CCN(c2cc(C(F)(F)F)c(C#N)c(Cl)n2)C1]

To a RBF add 3-cyano-2,6-dichloro-4-(trifluoromethyl) pyridine (123 mmol, 29.6 g) and EtOH (230 mL). Cool the mixture to 0° C. Add NaHCO$_3$ (368 mmol, 31 g) followed by a solution of methyl (R)-pyrrolidine-3-acetate hydrochloride (23 g, 123 mmol) in EtOH (230 mL). Allow the resulting mixture to warm to RT overnight. Evaporate the reaction mixture to dryness on a rotary evaporator. Add water (200 mL) and extract with MTBE (2×200 mL). Combine the extracts and evaporate to dryness. Purify by chromatography on silica gel using hexane/MTBE (gradient from 20 to 70%) to give the title compound (34.7 g, 99.89 mmol, 81% Yield) as a white solid. ES/MS (m/z): 348.0, 350.0 [M+H]+.

Preparation 4

Methyl 2-[(3R)-1-[5-cyano-6-[(2S)-2-methylazetidin-1-yl]-4-(trifluoromethyl)-2-pyridyl]pyrrolidin-3-yl]acetate

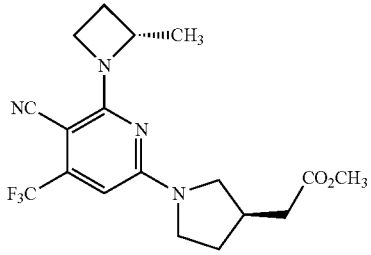 [SMILES: COC(=O)C[C@H]1CCN(c2cc(C(F)(F)F)c(C#N)c(N3CC[C@@H]3C)n2)C1]

To a RBF add methyl 2-[(3R)-1-[6-chloro-5-cyano-4-(trifluoromethyl)-2-pyridyl]pyrrolidin-3-yl]acetate (25.5 g, 73.3 mmol), [(1R,4S)-7,7-dimethyl-2-oxo-norbornan-1-yl]methanesulfonate (2S)-2-methylazetidin-1-ium salt (88.0 mmol, 26.7 g), MeOH (255 mL), and NaHCO$_3$ (220 mmol, 18.5 g). Stir the mixture at 65° C. for 16 h. Add [(1R,4S)-7,7-dimethyl-2-oxo-norbornan-1-yl]methanesulfonate (2S)-2-methylazetidin-1-ium salt (22.0 mmol, 6.68 g) and NaHCO$_3$ (147 mmol, 12.3 g) and continue stirring for 32 h. Remove the solvent on a rotary evaporator. To the residue add water (300 mL) and extract with MTBE (2×200 mL). Combine the extracts and dry over anhydrous MgSO$_4$, filter through silica gel, and concentrate to dryness to give the title compound (28.0 g, 73.2 mmol, 99% Yield) as a white solid. ES/MS (m/z): 383.2 [M+H]+.

Preparation 5

Methyl 2-[1-[6-chloro-5-cyano-4-(trifluoromethyl)-2-pyridyl]azetidin-3-yl]acetate

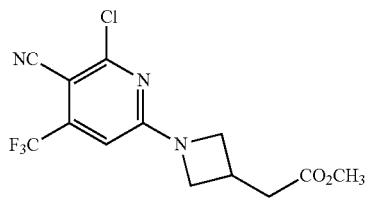 [SMILES: COC(=O)CC1CN(c2cc(C(F)(F)F)c(C#N)c(Cl)n2)C1]

To a solution of 3-cyano-2,6-dichloro-4-(trifluoromethyl)pyridine (500 mg, 2.03 mmol) in EtOH (15 mL) add NaHCO$_3$ (0.549 g, 6.51 mmol) and methyl 2-(azetidin-3-yl)acetate trifluoroacetic acid salt (0.494 g, 2.03 mmol). Stir the mixture at RT for 16 h. Dilute the reaction mixture with sat. aq. NaCl solution (30 mL). Extract with EtOAc (20 mL×3). Combine the extracts and wash with sat. aq. NaCl solution (30 mL), dry over anhydrous Na$_2$SO$_4$, filter, and concentrate. Purify the residue by column chromatography on silica gel eluting with EtOAc in petroleum ether (gradient 0-30%) to give the title compound (470 mg, 1.41 mmol, 66% Yield) as a white solid. ES/MS (m/z)=333.9 [M+H]+.

Preparation 6

Methyl 2-[1-[5-cyano-6-[(2S)-2-methylazetidin-1-yl]-4-(trifluoromethyl)-2-pyridyl]azetidin-3-yl]acetate

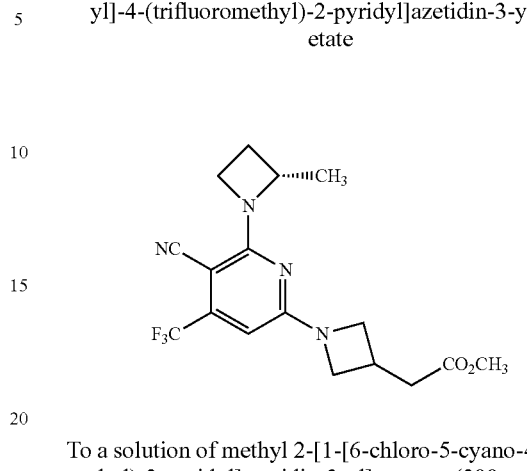

To a solution of methyl 2-[1-[6-chloro-5-cyano-4-(trifluoromethyl)-2-pyridyl]azetidin-3-yl]acetate (200 mg, 0.569 mmol) in EtOH (6 mL) add NaHCO$_3$ (0.173 g, 2.05 mmol) and [(1R,4S)-7,7-dimethyl-2-oxo-norbornan-1-yl]methanesulfonate (2S)-2-methylazetidin-1-ium salt (0.194 g, 0.626 mmol). Heat the mixture to 80° C. for 16 h. Dilute with water (50 mL) and extract with EtOAc (40 mL×3). Combine the extracts and wash with sat. aq. NaCl solution (50 mL), dry over anhydrous Na$_2$SO$_4$ filter and concentrate. Purify the residue by column chromatography on silica gel (0%-10%, EtOAc in petroleum ether) to give the title compound (176 mg, 0.46 mmol, 77% Yield) as a white solid. ES/MS (m/z): 383.1 [M+H]+.

Example 1

2-[(3R)-1-[5-cyano-6-[(2S)-2-methylazetidin-1-yl]-4-(trifluoromethyl)-2-pyridyl]pyrrolidin-3-yl]acetic Acid

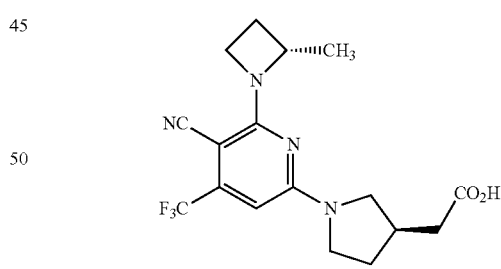

To a RBF add methyl 2-[(3R)-1-[5-cyano-6-[(2S)-2-methylazetidin-1-yl]-4-(trifluoromethyl)-2-pyridyl]pyrrolidin-3-yl]acetate (26.5 g, 69.3 mmol), MeOH (265 mL), and 2 M aq. NaOH solution (416 mmol, 208 mL). Stir the mixture at 60° C. for 3 h. Cool to RT and remove MeOH on a rotary evaporator. Acidify the aqueous phase to pH 3-4 using concentrated aq. HCl. Extract with EtOAc (400 mL). Wash the organic layer with water (200 mL), dry over anhydrous MgSO$_4$, filter, and concentrate to dryness to give the title compound (22.5 g, 61.11 mmol, 88% Yield) as a white foam. ES/MS (m/z): 369.2 [M+H]+.

Example 2

2-[1-[5-cyano-6-[(2S)-2-methylazetidin-1-yl]-4-(trifluoromethyl)-2-pyridyl]azetidin-3-yl]acetic Acid

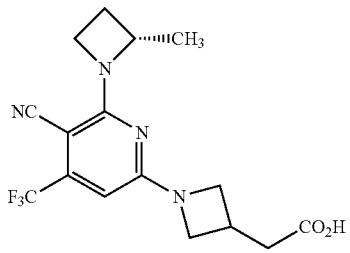 [SMILES: C[C@H]1CCN1c1nc(N2CC(CC(=O)O)C2)cc(C(F)(F)F)c1C#N]

To a mixture of methyl 2-[1-[5-cyano-6-[(2S)-2-methylazetidin-1-yl]-4-(trifluoromethyl)-2-pyridyl]azetidin-3-yl]acetate (176 mg, 0.478 mmol) in THF (5.00 mL) and water (1.00 mL) add LiOH (0.04 g, 0.955 mmol). Stir the resulting mixture at RT for 2 h. Dilute with EtOAc (4 mL) and extract the aqueous layer with EtOAc (2 mL×3). Combine the organic extracts and wash with sat. aq. NaCl solution (3 mL×2), dry over anhydrous $Na_2SO_4$, filter, concentrate to afford the title compound (128 mg, 0.36 mmol, 78% Yield) as a white solid. ES/MS (m/z) 354.9 [M+H]+.

Assays

KHK Enzyme Activity Assay for Human KHK-C and Human KHK-A

The intrinsic potency of the compounds may be measured using an enzymatic assay which measures the production of F P. Compounds are prepared in DMSO and tested in a 10-point concentration curve, to create 3-fold serial dilutions of the compounds in a 96-well plate ranging from 20 µM to 1.02 nM. Enzyme is prepared in assay buffer [50 mM 4-(2-hydroxyethyl)piperazine-1-ethanesulfonic acid (HEPES), 10 mM potassium chloride, 100 mM magnesium chloride, 2 mM tris(2-carboxyethyl)phosphine (TCEP), 0.01% n-octyl glucoside] and incubated with compounds at RT for 15 min. The reaction is carried out in 100 µL volumes containing substrate concentrations of fructose (250 µM for KHK-C assay and 1.25 mM for KHK-A assay) and ATP (150 µM for both isoforms); which are further incubated at RT for 20 min. The reaction is then halted by the addition of stop buffer; consisting of 0.2% formic acid and 1 µg/ml $^{13}C_6$-fructose-6-phosphate ($^{13}C_6$-F6P) internal standard. Plates are stored in −20° C. until RapidFire MS analysis. RapidFire MS Analysis for Quantitation of F1P:

An Agilent 300 RapidFire automated extraction system (Agilent, Santa Clara, Calif.) with three HPLC quaternary pumps is coupled to an Agilent 6495 triple quadrupole mass spectrometer (Agilent Technologies, Santa Clara, Calif.) equipped with an electrospray ionization (ESI) interface source. The RapidFire Mass Spec system is equipped with a reusable RapidFire C18 (type C) solid-phase extraction (SPE) cartridge (G9205A).

Solvent A, used for sample loading and washing, is 6 mM octylamine (Acros Organics 129495000) brought to pH 5.0 using acetic acid. Solvent B, used for sample elution, is 20% water in ACN containing 0.1% formic acid. Samples are sequentially analyzed by aspirating 10 µL onto the collection loop under vacuum directly from multiwell plates. The 10 µL of sample is loaded onto the C18 cartridge and washed using solvent A at a flow rate of 1.25 mL/min for 5000 ms. The retained analytes are then eluted to the mass spectrometer using solvent B at a flow rate of 1.25 mL/min for 5000 ms. The system is re-equilibrated using solvent A at a flow rate of 1.25 mL/min for 2000 ms.

The triple quadrupole mass spectrometer is equipped with an ESI source and analytes are monitored using selected reaction monitoring (SRM) in negative mode [M−H]−. F1P is monitored at m/z 259.02/96.9 and $^{13}C_6$-fructose-6-phosphate is monitored at m/z 264.99/97. The area ratio values for F1P is calculated using $^{13}C_6$-fructose-6-phosphate as internal standard.

The compounds of Examples 1 and 2 were tested essentially as described above:

TABLE 1

| Example Number | hKHK-C $IC_{50}$ (nM) | hKHK-A $IC_{50}$ (nM) |
| --- | --- | --- |
| 1 | 9 | 19 |
| 2 | 27 | 37 |

These results demonstrate that the compounds of Examples 1 and 2 inhibit the enzymatic activity of both KHK-C and KHK-A.

KHK Cellular Activity Assay

Potency can be measured using a cellular assay for the inhibition of the conversion of Fructose to F1P by cellular KHK. HepG2 cells are plated on 96-well cell culture plates in growth media [Dulbecco's Modified Eagle's medium (DMEM) high glucose, 10% heat-inactivated fetal bovine serum (HI FBS), 1× Penicillin/streptomycin] and allowed to attach overnight in a 37° C. incubator. The growth media is washed and replaced with assay media consisting of Gibco OptiMEM 1 Reduced Serum Medium, 0.1% Casein, 8.33 mM D-Fructose-$^{13}C_6$, and compound concentrations ranging from 100 µM to 0.0051 µM (10-point concentration curve). Plates are incubated at 37° C. for 3 h, after which assay media is aspirated from the cell wells. Stop solution consisting of 80% methanol, 2 mM ammonium acetate, and 50 ng/mL fructose-6-phosphate-$^{13}C_6$ is then added to the cells. Plates are stored in −20° C. until RapidFire MS analysis (described above).

The compounds of Examples 1 and 2 were tested essentially as described above:

TABLE 2

| Example Number | HepG2 $IC_{50}$ |
| --- | --- |
| 1 | 127 |
| 2 | 316 |

These results demonstrate that the compounds of Examples 1 and 2 inhibit the metabolism of fructose to F1P.

Liquid Chromatograph with Tandem Mass Spectrometry (LC-MS/MS) Method for Pharmacokinetic Assays: Samples are extracted using a protein precipitation by adding 180 µL of MeOH:ACN (1:1, v/v) containing an internal standard and 25 µL (rodent samples) or 50 µL(non-rodent samples) of plasma. Samples are then diluted with Methanol:Water (1:1, v/v) to get concentrations within standard curve range. Diluted samples are analyzed by LC-MS/MS using a Sciex API 4000 triple quadrupole mass spectrometer (Applied Biosystems/MDS; Foster City, Calif.) equipped with a TurbolonSpray interface, and operated in positive ion mode. The analytes are chromatographically separated using a Thermo Betasil C18 5 um 20×2.1 mm Javelin column (rodent samples) or Advantage ECHIELON C18 4 um 20 mm×2.1 mm ID column (non-rodent samples). LC conditions are Water/1 M ammonium bicarbonate, (2000:10, v/v) (Mobile Phase A), and MeOH/1 M ammonium bicarbonate, (2000:10, v/v) (Mobile Phase B).

Pharmacokinetics in Mice

The in vivo pharmacokinetic properties and involvement of OATP A/1B transporter in disposition of Example 1 are demonstrated using FVB wild type mice and OATP A/1B knockout mice (Taconic #10707) (fasted; n=4/genotype). Example 1 is administered by a single intravenous (IV; 1 mg/kg; volume of 1 mL/kg) dose in vehicle. Blood is collected from each animal at 0, 0.08, 0.25, 0.5, 1, 2, 4, 8, 12, and 24 h post-dosage. Liver, spleen, and pancreas is collected, weighed and perfused at 24 h post-dosage. The plasma and tissue concentrations of Example 1 are determined by a LC-MS/MS method as described above.

In FVB mice, Example 1 has 5.43 hour half-life, a mean clearance of 6.91 mL/hr/kg, a volume of distribution of 2.74 L/kg, with a mean liver unbound partition coefficient ($K_{puu}$) of 67.5. In OATP1A/1B knockout mice, Example 1 has 9.36 hour half-life, a mean clearance of 1.34 mL/hr/kg, a volume of distribution of 0.986 L/kg, with a mean liver unbound partition coefficient ($K_{puu}$) of 24.2. This data shows OATP is involved in the hepatic uptake of Example 1 in the mouse and that involvement of this transporter affects clearance.

Pharmacokinetics in Dogs

The in vivo pharmacokinetic properties of Example 1 are demonstrated using Beagle Dogs (fed, n=3-4). Example 1 is administered by a single oral (PO; 3 mg/kg; volume of 2 mL/kg) or intravenous (IV; 1 mg/kg; volume of 1 mL/kg) dose in vehicle. Blood is collected from each animal at 0, 0.03 (IV group only), 0.08 (IV), 0.25, 0.5, 1, 2, 4, 8, 12, 24, 32 (IV), 48 (IV), and 72 (IV) h post-dosage. The plasma concentrations of Example 1 are determined by a LC-MS/MS method as described above.

For PO doses, Example 1 mean half-life is 6.9 hours and bioavailability is ~93%. For IV doses, Example 1 mean half-life is 7.4 hours and the mean clearance is 2.52 mL/hr/kg with a low volume of distribution (1.33 L/kg). This data shows Example 1 has low total clearance, low volume of distribution and high oral bioavailability in dogs.

The characterization of major elimination pathways in vivo are demonstrated using bile duct cannulated (BDC) Beagle Dogs (fed; n=3). Example 1 is administered by a single intravenous (IV; 1 mg/kg; volume of 1 mL/kg) dose in vehicle. Blood is collected from each animal at 0, 0.033, 0.083, 0.25, 0.5, 1, 2, 4, 8, 12, 24, 32, 48 and 72 h post-dosage. Bile is collected from each animal at 1, 2, 3, 4, 5, 6, 12, 18, 24, 32, 48 and 72 h post-dosage. Urine is collected at 12, 24, 48, and 72 h and feces collected at 24, 48, and 72 h post-dosage. The plasma, bile, urine and feces concentrations of Example 1 are determined by a LC-MS/MS method as described above.

Example 1 mean half-life is 2.9 hours and the mean clearance is 4.69 mL/hr/kg with a low volume of distribution (0.546 L/kg). Example 1 urine levels are negligible and ~10% of the administered IV dose is recovered in bile. This data shows Example 1 has low renal and biliary elimination. Overall, the elimination half-life in bile cannulated dogs, 2.9 hr, is faster than the half-life measured in intact dogs, 7.4 hr, suggesting enterohepatic recirculation.

Pharmacokinetics in Cynomolgus Monkeys

The in vivo pharmacokinetic properties of Example 1 are demonstrated using cynomolgus monkeys. The compounds is administered by a single oral (PO; 10 mg/kg; volume of 5 mL/kg) dose in vehicle. Blood is collected from each animal at 0, 0.25, 0.5, 1, 2, 4, 8, 12, 24, 32, 48, and 72 h post-dosage. The plasma concentrations of Example 1 are determined by a LC-MS/MS method as described above.

Example 1 mean half-life is 15.3 hours. This data shows Example 1 is orally bioavailable and slowly eliminated in monkeys.

Intrinsic Clearance in Human Hepatocytes (−/+ABT)

This method is intended to identify in vitro metabolic clearance by substrate depletion in hepatocytes. Incubation in the presence and absence of ABT, a pan-CYP450 enzyme inhibitor, is used to estimate the contribution of CYP-mediated metabolism. Cryopreserved human hepatocytes are thawed at 37° C., spun down and reconstituted in hepatocyte maintenance media to a density of $1 \times 10^6$ viable cells/mL. To a pre-warmed 96-well plate, 196 μL of the hepatocyte suspension is added to each well. The cells are pre-incubated with and without ABT as follows: for ABT pre-incubation, 2 μL of 100 mM ABT solution is added (2 μL of media without ABT is added to control samples), and the plate incubated at 37° C. for 30 min under constant shaking (~600 rpm). Following, 2 μL of a 30 μM stock solution of test article is added and at 0, 15, 30, 60, 120, 240 min 20 μL aliquots are taken and quenched by transfer to ACN containing internal standard. Following centrifugation at 4000 rpm for 30 min, supernatant concentrations are determined by LC-MS/MS. Clearance is calculated from the slope of % compound remaining over time.

Clearance of Example 1 is inhibited by ABT by ~12% in human hepatocytes, suggesting limited involvement of CYP enzymes in the hepatic clearance of Example 1.

Inhibition of OATP1B1 and OATP1B3

The OATP1B1, OATP1B3, and vector control (VC) cells are grown in 5% $CO_2$ at 37° C. in a humidified atmosphere in DMEM supplemented with 10% FBS, 50 μg/mL gentamycin, and 5 μg/mL blasticidin. The cells are seeded in 24-well BioCoat Poly-D-Lysine plates. The cells are treated with 5 mM sodium butyrate in supplemented DMEM 24 h prior to experimentation. Cell cultures are washed twice with pre-warmed PBS prior to experimentation. After washing, all cell types are incubated for 30 min at 37° C. in 200 μL buffer, buffer plus varying concentration of test article, or with appropriate positive control inhibitor. Based upon preliminary data concentrations from 0.025 to 12.5 μM for OATP1B1 and 0.20 to 100 μM for OATP1B3 (nominal) are tested. At the start of the preincubation, 50 L of buffer is removed for determination of in-well test article concentrations by LC-MS/MS. Following the pre-incubation period, the buffer is removed. Experiments are initiated by the addition of 200 μL substrate solution (400 nM rosuvastatin total, including 1.4 nM tritiated rosuvastatin). Incubations are performed with and without inhibitor. Positive control inhibitor used for each cell line is 50 M rifamycin SV. Experiments are carried out for 1 min at 37° C., at which the reaction is stopped and washed with the addition of 1000 μL ice cold PBS per well. Each well is then aspirated and washed two additional times with ice cold PBS. Cells in each well are lysed in 400 μL 1% Triton X 100 in PBS (by volume). Samples are taken from each well from plates to count for radioactivity and protein concentration in each well is determined by bicinchoninic acid method. $IC_{50}$ values are determined by fitting the data using GraphPad Prism. Nominal concentrations are converted to measured concentrations prior to fitting.

Example 1 inhibited OATP1B1 more potently than OATP1B3, with $IC_{50}$ values of 0.12 and 5.5 μM, respectively.

I claim:

1. A compound of the formula:

Formula I

[Chemical structure: pyridine with NC, F₃C, 2-methylazetidinyl, and azetidinyl-(CH₂)ₙ-CO₂H substituents]

wherein n is 1 or 2;
or a pharmaceutically acceptable salt thereof.

2. The compound according to claim 1 wherein n is 1, or a pharmaceutically acceptable salt thereof.

3. The compound according to claim 2 wherein the compound is:

[Chemical structure with stereochemistry shown]

or a pharmaceutically acceptable salt thereof.

4. The compound according to claim 1 wherein n is 2, or a pharmaceutically acceptable salt thereof.

5. The compound according to claim 4 wherein the compound is:

[Chemical structure with pyrrolidine ring]

or a pharmaceutically acceptable salt thereof.

6. The compound according to claim 5 wherein the compound is:

[Chemical structure with defined stereochemistry]

or a pharmaceutically acceptable salt thereof.

7. A method of treating type 2 diabetes mellitus in a patient comprising administering to a patient in need of such treatment an effective amount of a compound of claim 1, or a pharmaceutically acceptable salt thereof.

8. A method of treating heart failure in a patient comprising administering to a patient in need of such treatment an effective amount of a compound of claim 1, or a pharmaceutically acceptable salt thereof.

9. A method of treating diabetic kidney disease in a patient, comprising administering to a patient in need of such treatment an effective amount of a compound of claim 1, or a pharmaceutically acceptable salt thereof.

10. A method of treating non-alcoholic steatohepatitis in a patient, comprising administering to a patient in need of such treatment an effective amount of a compound of claim 1, or a pharmaceutically acceptable salt thereof.

11. A pharmaceutical composition comprising a compound, or a pharmaceutically acceptable salt thereof, according to claim 1, with one or more pharmaceutically acceptable carriers, diluents, or excipients.

12. A process for preparing a pharmaceutical composition comprising admixing a compound, or a pharmaceutically acceptable salt thereof, according to claim 1, with one or more pharmaceutically acceptable carriers, diluents, or excipients.

* * * * *

UNITED STATES PATENT AND TRADEMARK OFFICE
CERTIFICATE OF CORRECTION

PATENT NO. : 10,781,212 B2
APPLICATION NO. : 16/555075
DATED : September 22, 2020
INVENTOR(S) : Timothy Barrett Durham It is certified that error appears in the above-identified patent and that said Letters Patent is hereby corrected as shown below:

On the Title Page

Column 2, item [56], Line 3 Delete "G X.," and insert -- G.X., --, therefor.

Column 2, item [56], Line 4 Delete "C.S. (2017)" and insert -- C. B. (2017). --, therefor.

Signed and Sealed this
Seventeenth Day of November, 2020

Andrei Iancu
*Director of the United States Patent and Trademark Office*